United States Patent
Lutz et al.

(10) Patent No.: US 7,586,095 B2
(45) Date of Patent: Sep. 8, 2009

(54) X-RAY DETECTOR AND DETECTOR MODULE

(75) Inventors: Helmut Lutz, Hausen (DE); Claus Pohan, Baiersdorf (DE); Gottfried Tschöpa, Rednitzhembach (DE)

(73) Assignee: Siemens Aktiengesellschaft, Munich (DE)

( * ) Notice: Subject to any disclaimer, the term of this patent is extended or adjusted under 35 U.S.C. 154(b) by 16 days.

(21) Appl. No.: 11/806,162

(22) Filed: May 30, 2007

(65) Prior Publication Data

US 2007/0280410 A1   Dec. 6, 2007

(30) Foreign Application Priority Data

May 31, 2006   (DE) ................ 10 2006 025 765

(51) Int. Cl.
*G01T 1/24* (2006.01)
(52) U.S. Cl. .................................. 250/370.09
(58) Field of Classification Search ........... 250/370.01–370.15; 378/98.6, 98.7, 98.8
See application file for complete search history.

(56) References Cited

U.S. PATENT DOCUMENTS

| 5,444,752 | A | 8/1995 | Dobbs |
| 7,104,687 | B2 * | 9/2006 | Okamura et al. ............ 378/200 |
| 2005/0067579 | A1 * | 3/2005 | Tsuchiya et al. ....... 250/370.15 |
| 2005/0117698 | A1 | 6/2005 | Lacey |
| 2005/0287008 | A1 | 12/2005 | Joshi |

FOREIGN PATENT DOCUMENTS

| DE | 195 81 493 | 6/1997 |
| DE | 101 35 288 | 2/2003 |
| DE | 102004058299 A1 | 7/2005 |
| WO | WO 03046610 A1 | 6/2003 |

* cited by examiner

*Primary Examiner*—David P Porta
*Assistant Examiner*—Kiho Kim
(74) *Attorney, Agent, or Firm*—Harness, Dickey & Pierce, P.L.C.

(57) ABSTRACT

An X-ray detector includes a plurality of detector modules arranged in the interior of a detector housing. In at least one embodiment, the detector housing is designed to supply a coolant into the interior. In at least one embodiment, in order to cool the detector modules, each is provided with a heat sink element, which extends into the interior, through which a coolant flows during operation.

12 Claims, 2 Drawing Sheets

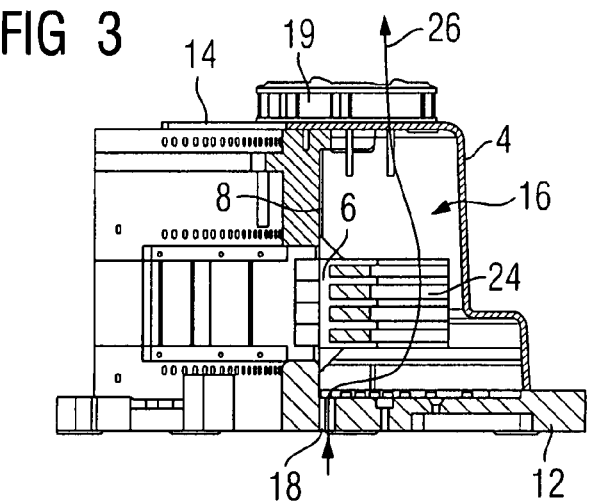
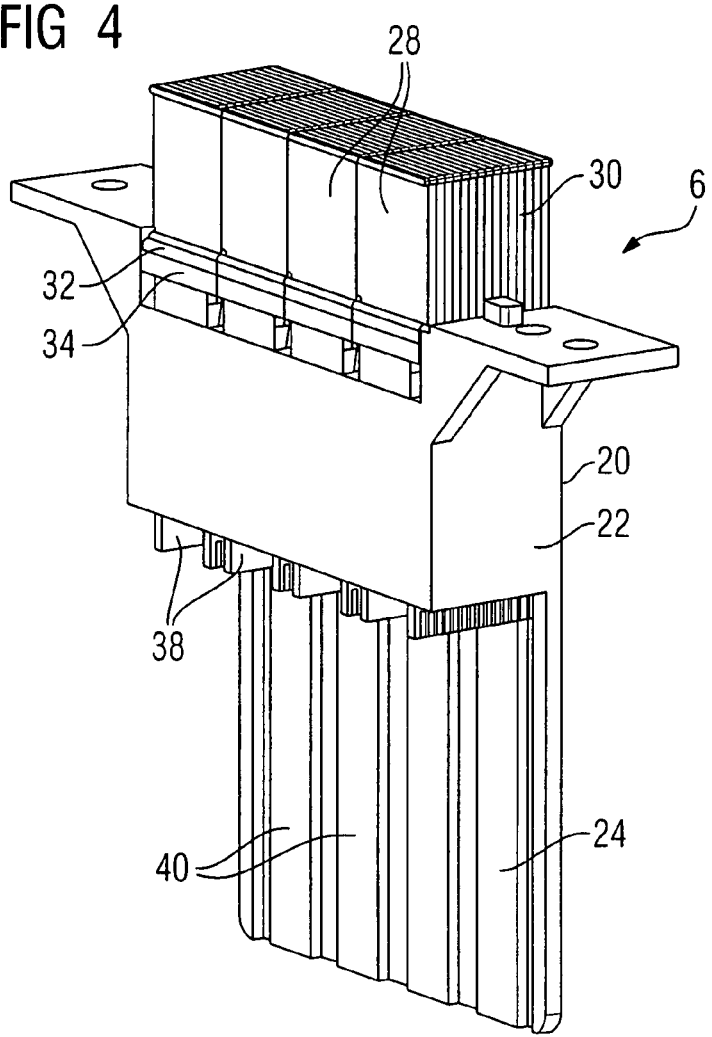

X-RAY DETECTOR AND DETECTOR MODULE

PRIORITY STATEMENT

The present application hereby claims priority under 35 U.S.C. §119 on German patent application number DE 10 2006 025 765.0 filed May 31, 2006, the entire contents of which is hereby incorporated herein by reference.

FIELD

Embodiments of the invention generally relate to an X-ray detector including a plurality of detector modules arranged in the interior of a detector housing. For example, it may relate to one where the detector housing is designed to supply a coolant into the interior. Embodiments of the invention furthermore generally relate to a detector module for such an X-ray detector.

BACKGROUND

A digital detector is disclosed, for example, by DE 101 35 288 U1 and is used in an X-ray computer tomograph. An X-ray detector conventionally comprises a plurality of detector modules, which are arranged in the manner of an array or a matrix in a housing. The detector modules are formed by at least one detector element.

Each detector element has a sensor element on the front end, which registers the X-rays incident on the detector element. The sensor element generally comprises a scintillator, which is stimulated by the γ quanta of the X-radiation and generates light, as well as a downstream photodiode arrangement for measuring the quantity of the light generated. A collimator, by which scattered radiation components are absorbed, is conventionally arranged in front of the scintillator.

The detector element furthermore comprises readout electronics having a plurality of electronic components. The sensor element and the electronic components are, for example, arranged on a printed circuit board of the detector element.

SUMMARY

The signals of the sensor element are evaluated or digitized in the electronic components. A non-negligible heat loss, which needs to be dissipated, is generated during operation in the detector components. Strong heating or heat stagnation, or strong temperature variations, may lead to malfunction of the electronic components and therefore of the detector module. Applicants have recognized that a difficulty in this case is that both the electronic components and the converter elements of the detector, such as the scintillator and the photodiode arrangement, have temperature-dependent properties and must be kept as thermally stable as possible, since certain temperature changes can lead to image artifacts.

In at least one embodiment, the invention ensures effective cooling of the detector modules of an X-ray detector.

At least one embodiment of the invention is directed to an X-ray detector, comprising a plurality of detector modules arranged in the interior of a detector housing, the detector housing being designed to supply a coolant into the interior, characterized in that the individual detector modules each have a heat sink element which extends into the interior through which a coolant flows during operation.

At least one embodiment of the invention is based on the idea that particularly effective cooling of the detector modules of the X-ray detector is facilitated if the heat loss generated in the electronic components of the detector modules is conducted owing to a temperature difference into a cooled heat sink element, which is in contact with the components. The heat sink element is exposed to a convective coolant flow, the coolant being at a lower temperature than the components. The components' heat loss diffusing into the heat sink element is thereby transported away continuously by the coolant.

The heat sink element extents into the interior through which the coolant flows, so that a maximally large surface of the heat sink element is exposed to the coolant, which leads to particularly effective cooling. In particular, the amount of coolant can therefore be kept small. The arrangement and alignment of the heat sink elements furthermore means that the electronic components of the detector module are exposed little or not at all to the coolant, so that their temperature level remains stable during operation.

Rapid temperature changes in the detector modules, which can lead to image artifacts, are particularly effectively restricted if the heat sink element preferably comprises a module housing, in which the detector module's components to be cooled are arranged. The module housing prevents the electronic components from being exposed directly to the coolant.

The components to be cooled are preferably encapsulated by the module housing. Encapsulation is in this case intended to mean that the module housing encases the detector module so that it protects the components against direct convective cooling. The cooling of the components thus takes place exclusively by transferring heat to the relatively cool heat sink element, a part of which is also the module housing. Owing to the indirect cooling of the components and the compensating thermal buffer of the module housing, temperature discontinuities of the coolant do not per se act directly on the sensitive components. Furthermore, the encapsulation may also be configured so that the components are likewise simultaneously protected by the module housing against dust build-ups.

According to an example configuration of at least one embodiment, each of the detector modules comprises at least one detector element directed toward a front detection side of the detector housing and the heat sink elements extend rearward in an opposite direction. In this configuration, the detector housing's interior through which the coolant flows is utilized particularly effectively in order to make the heat sink elements as large as possible, and thereby to increase the thermal transfer between the heat sink elements and the coolant.

There is particularly large-area and therefore effective cooling if the heat sink elements preferably each comprise a plate, which extends in the interior.

The dissipation of heat from the plate of the heat sink element is furthermore improved if the plate preferably has a profiled surface. For example, the surface of the plate is provided with alternate indentations and elevations whose shape, size and alignment are selected so that particularly favorable thermal transfer is achieved.

Expediently, the heat sink element is made of metal, in particular aluminum. Metals have a very good thermal conductivity, which makes them particularly suitable for use as a heat sink element.

According to an example variant of at least one embodiment, the detector housing has openings for the coolant along the detector modules. The openings are arranged in particular on a base plate and a cover plate of the detector housing, which plates adjoin the front detection side. A coolant flow, which flows around the heat sink elements lying in the interior, is thereby generated in the detector housing. It is particularly advantageous in this case for the distance between the bottom and cover plates to be relatively small, so that there is an insignificant temperature gradient in the flow direction, with the result that particularly uniform cooling of all regions of the heat sink elements is ensured.

According to another example variant of at least one embodiment, at least one fan for supplying air as a coolant is provided on the detector housing. So that more space in the detector housing is available for the heat sink elements, the fan or a number of fans are arranged in particular on an outer side of the bottom or cover plate. The fan or fans are positioned in the vicinity of the openings, so that ambient air is blown or sucked into the openings and the flow in the housing is therefore generated.

A detector module for an X-ray detector, according to at least one embodiment of the invention, includes at least one component to be cooled. The component is in thermally conductive contact with a heat sink element, which heat sink element is designed so that it is exposed to a coolant during operation. The advantages and preferred embodiments mentioned in respect of the X-ray detector can be applied accordingly to the detector module.

BRIEF DESCRIPTION OF THE DRAWINGS

An example embodiment of the invention will be explained in more detail with the aid of the drawings, in which:

FIG. 3 shows a section in the plane BB according to FIG. 1, and FIG. 4 shows a perspective representation of a detector module.

Figure 1:
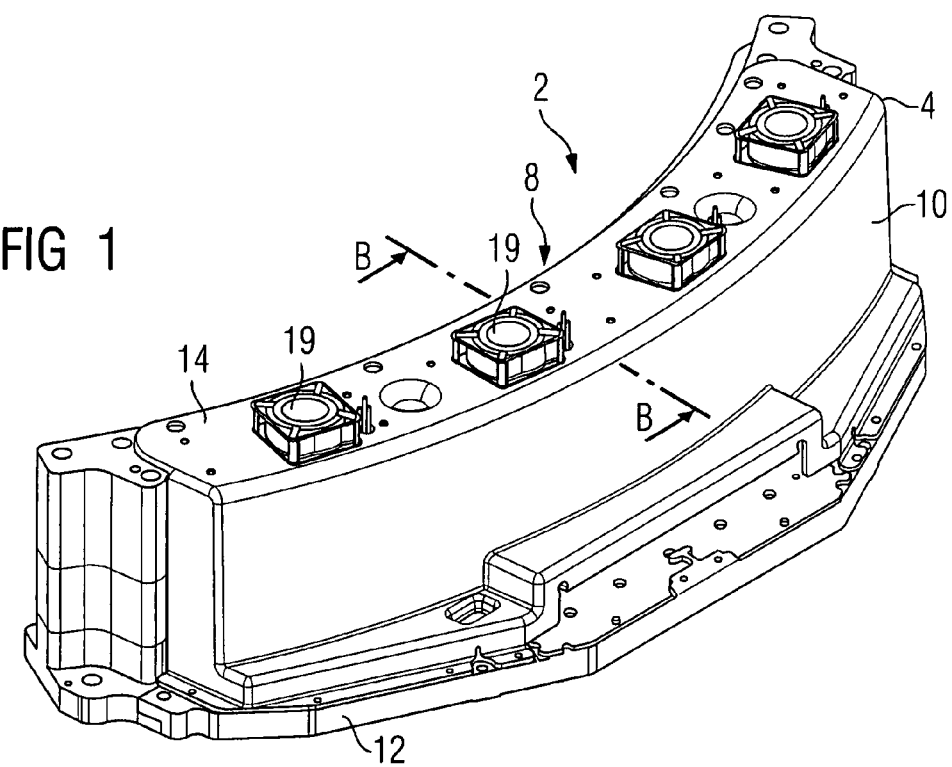
FIG. 1 shows a perspective representation of an X-ray detector.

Reference numerals which are the same have the same meaning in the figures.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows a digital X-ray detector 2 which, in particular, is used for imaging in a computer tomograph. The X-ray detector 2 has a detector housing 4, in which a multiplicity of detector modules 6 (cf. FIGS. 2 to 4) are arranged. The X-ray detector 2 has an arc-shaped front detection side 8, on which the detector modules 6 are arranged in a row (cf. FIG. 2). The detection side 8 is directed at an X-ray source (not shown here) and it is struck by X-rays from the beam source. A rear side 10 of the detector housing 4 is arranged on the opposite side. A base plate 12 and a cover plate 14 adjoin the detection side 8 and the rear side 10. Fans 19, which in this example embodiment suck in air as a coolant and thereby generate a coolant flow in the housing 4, are provided on the cover plate 14.

Figure 2:
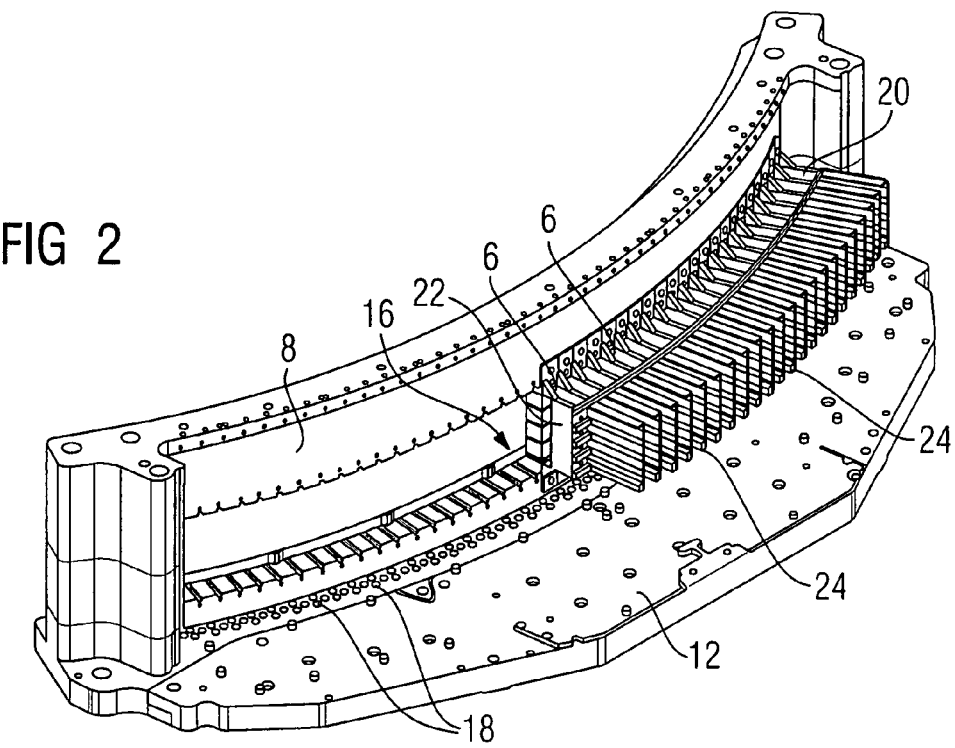
FIG. 2 shows a perspective representation of an interior of the open X-ray detector according to FIG. 1.

As can be seen from FIG. 2, the detector housing 4 encloses an interior 16 in which the detector modules 6 extend downward. Openings 18, through which the cooling air flows into the housing 4, are provided on the base plate 12. The openings 18 are arranged along the detector modules 6 arranged in a row, so that the cooling air flows into the housing 4 directly below the detector modules 6 and therefore effectively cools the detector modules 6. Corresponding openings (not shown) for the cooling air to flow out of the housing 4 are provided below the fans 19 on the cover plate 14.

The detector modules 6 are respectively encased by a heat sink element 20, which includes a module housing 22 and a plate 24. The plates 24 of the individual detector modules 6 extend into the interior 16 in the direction toward the rear wall 10, and are cooled convectively by the cooling air flowing through. Further details regarding the structure and function of the detector modules 6 can be found in FIG. 4.

FIG. 3 shows a section through the plane BB according to FIG. 1. The coolant air flows through the openings 18 in the base plate 12 into the housing 4, which is indicated by the arrow 26. The cooling air flows around the plate 24 of the detector module 6 on the way to the cover plate 14 and cools it convectively. The air for cooling the detector modules 6 is sucked in by the fan 19 and therefore sent out of the housing 4. By virtue of the fan 19, a forced convective flow is set up in the interior 16, which leads to constant supply of further air into the housing 4. As an alternative, the fan 19 may also be designed so that it blows the air into the housing 4 through the openings in the cover plate 14 and the air then flows out of the interior 16 through the openings 18 in the base plate 12.

A detector module 6 for the X-ray detector 2, including a plurality of detector elements 28 arranged parallel, is shown in FIG. 4. Each of the detector elements 28 has a collimator 30 preceding it. The collimators 30 include a multiplicity of collimator plates, which are oriented in a radial direction toward a focal point of the X-radiation source. The collimators 30 are arranged on a scintillator 32 which is designed in the manner of a scintillator ceramic, for example of gadolinium oxisulfide, or a scintillator crystal such as cesium iodide or cadmium tungstate. The X-rays incident on the scintillator 32 generate a light flash, which is converted into an electrical signal by a photomultiplier, in this example embodiment a photodiode arrangement 34. The scintillator 32 and the photodiode arrangement 34 therefore form a sensor element, which registers the X-rays.

The photodiode arrangement 34 is fastened on a printed circuit board, which is covered here by the heat sink element 20. The printed circuit board forms a kind of platform, on which further electronic components for digitizing and evaluating the signal of the sensor element are arranged. A connector 38, which is used to forward the digitized measurement values, is provided at the end of each printed circuit board.

The heat loss generated in the electronic components must be transported away in order to avoid interfering with the operation of the X-ray detector 2. Since the electronic components are temperature-sensitive and the quality of the images generated by means of the X-ray detector 2 are compromised in the event of temperature discontinuities, the components are encapsulated by the module housing 22 of the heat sink element 20 that they are not exposed directly to the coolant. In this way the electronic components to be cooled lie in direct contact with the heat sink element 20, so that their heat loss can diffuse into the heat sink element 20.

The heat sink element 20 is made from a thermally conductive metal, in this example embodiment aluminum. The heat loss is therefore conducted from the region of contact with the heated components further into the plate 24, and is distributed uniformly in the heat sink element 20. Since the heat sink element 20 is exposed to the cooling air flow, this heat is continuously dissipated. In order to achieve a large quantity of heat transported away, without having to increase the cooling air rate, the plate 24 is provided with cooling fins 40 which form a profiled surface. The contact area between the heat sink element 20 and the cooling air is therefore increased, the effect of which is that more heat is dissipated per unit time. The heat sink element 20 is thereby cooled, and is capable of absorbing further heat from the components.

The heat sink element 20 constitutes a thermal buffer, which shields the components against the cooling air. By virtue of this indirect cooling, temperature discontinuities of the cooling air are attenuated so that the function of the temperature-sensitive components is not compromised and the image quality is preserved.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray detector, comprising:
    a plurality of detector modules arranged in an interior of a detector housing, the individual detector modules each including a heat sink element, which extends into the interior of the detector housing, the heat sink being configured to flow a coolant around an exterior of the heat sink element during operation, wherein
    the heat sink element includes a module housing, in which components of the detector module to be cooled are arranged, and a plate that extends into the interior of the detector, and
    the components to be cooled are arranged on a printed circuit board and are encapsulated by the module housing, and
    a connector is provided at an end of the printed circuit at a rear side of the module housing, the connector being arranged in front of the plate.

2. The X-ray detector as claimed in claim 1, wherein each of the detector modules includes at least one detector element directed toward a front detection side of the detector housing and the heat sink elements extend rearward in an opposite direction.

3. The X-ray detector as claimed in claim 1, wherein the plate includes a profiled surface.

4. The X-ray detector as claimed in claim 1, wherein the heat sink element is made of metal.

5. The X-ray detector as claimed in claim 4, wherein the metal is aluminum.

6. The X-ray detector as claimed in claim 1, wherein the detector housing includes openings for the coolant along the detector modules.

7. The X-ray detector as claimed in claim 1, wherein at least one fan for supplying air as a coolant is provided on the detector housing.

8. A detector module for an X-ray detector as claimed in claim 1, wherein
    the component are in thermally conductive contact with the heat sink element, the heat sink element being designed so that it is exposed to a coolant during operation.

9. The X-ray detector as claimed in claim 1, wherein each of the detector modules includes at least one detector element directed toward a front detection side of the detector housing and the heat sink elements extend rearward in an opposite direction.

10. A computer tomograph, comprising:
    the X-ray detector as claimed in claim 1.

11. An X-ray detector, comprising:
    a detector housing; and
    a plurality of detector modules, arranged in an interior of the detector housing, each of the plurality of detector modules including a heat sink element having a module housing that encapsulates components to be cooled and a plate extending from the module housing into the interior of the detector housing, wherein coolant flows around sides of the plate that extend into into the interior of the detector housing.

12. A computer tomograph, comprising: the X-ray detector as claimed in claim 11.

* * * * *